(12) United States Patent
Leng

(10) Patent No.: US 12,414,875 B1
(45) Date of Patent: Sep. 16, 2025

(54) ANTERIOR VITRECTOMY APPARATUS

(71) Applicant: Jason Leng, Chehalis, WA (US)

(72) Inventor: Jason Leng, Chehalis, WA (US)

( * ) Notice: Subject to any disclaimer, the term of this patent is extended or adjusted under 35 U.S.C. 154(b) by 120 days.

(21) Appl. No.: 18/517,679

(22) Filed: Nov. 22, 2023

Related U.S. Application Data

(63) Continuation-in-part of application No. 16/859,250, filed on Apr. 27, 2020, now abandoned.

(60) Provisional application No. 62/838,472, filed on Apr. 25, 2019.

(51) Int. Cl.
*A61F 9/007* (2006.01)
*A61B 90/30* (2016.01)
*A61B 17/00* (2006.01)

(52) U.S. Cl.
CPC .......... *A61F 9/00754* (2013.01); *A61B 90/30* (2016.02); *A61B 2017/00424* (2013.01); *A61B 2017/00544* (2013.01); *A61B 2017/00973* (2013.01); *A61B 2090/306* (2016.02); *A61B 2217/005* (2013.01); *A61B 2217/007* (2013.01)

(58) Field of Classification Search
CPC .......................... A61F 9/00754; A61F 9/00736
See application file for complete search history.

(56) References Cited

U.S. PATENT DOCUMENTS

| | | | |
|---|---|---|---|
| 2009/0082715 A1* | 3/2009 | Charles | A61F 9/00763 606/171 |
| 2016/0270957 A1* | 9/2016 | Easley | A61F 9/00736 |

* cited by examiner

*Primary Examiner* — Si Ming Ku
(74) *Attorney, Agent, or Firm* — John Rizvi; John Rizvi, P.A.—The Patent Professor®

(57) ABSTRACT

A portable, compact, standalone anterior vitrectomy apparatus includes a housing sized and configured to fit in the palm of a human hand. A vitrectomy cutter connectable to an air tubing connector in the housing via an air tubing. A pressure reservoir in the housing communicates with an air control valve which in turn communicates with the air tubing connector. An internal air compressor, arranged inside the housing, communicates with an air regulator for supplying compressed air to the pressure reservoir. A speed control switch controllably interface with the air control valve. A processor controllably interface with the speed control switch and control the air control valve through the speed control switch such that the air control valve delivers pulses of air from the pressure reservoir through the air control valve to drive the vitrectomy cutter.

20 Claims, 11 Drawing Sheets

ANTERIOR VITRECTOMY APPARATUS

CROSS-REFERENCE TO RELATED APPLICATION

This application is a Continuation-in-Part of U.S. patent application Ser. No. 16/859,250, filed on Apr. 27, 2020, which in turn claims the benefit of U.S. Provisional Patent Application No. 62/838,472, filed on Apr. 25, 2019, which are incorporated by reference herein in their entirety.

FIELD OF THE INVENTION

The present invention relates generally to medical devices, and more particularly, to a portable, compact, standalone anterior vitrectomy apparatus which can be used to cut vitreous humor from a subject's eye.

BACKGROUND OF THE INVENTION

The human eye is filled with a gel-type substance known as vitreous gel, or vitreous humor. Vitreous humor is a thick, colorless, gel-like fluid which fills the interior space of the eyeball between the lens and the retina and helps the eyeball maintain its generally spherical shape.

In some cases, it may be necessary or desirable to remove the vitreous humor from an eye. Such a procedure is known as a vitrectomy. Vitrectomy may facilitate access to repair or prevent retinal detachment, retinal tears, or severe proliferative retinopathy. Vitrectomy may also reduce loss of vision in the case of vitreous hemorrhage. In cataract surgery, any vitreous that migrates forward towards the front of the eye must be cut and removed to prevent vision loss.

Various types of vitrectomy devices are known in the art. These devices have different designs with various features. However, all vitrectomy devices have the same basic functional mechanism. These devices cut the vitreous humor out of the eye using a reciprocating cutting blade (driven either pneumatically or electrically), combined with a source of vacuum that removes the vitreous humor and irrigation which replaces the removed mass with fluid.

Conventional vitrectomy devices typically fall into two categories: posterior vitrectomy apparatus and anterior vitrectomy apparatus. Posterior vitrectomy apparatus are typically used for retinal and other surgeries which are performed at the back of the eye. These surgeries may be complex and may need to be combined with other retinal repairing tools such as fiber optic light sources, pneumatic scissors, etc. Anterior vitrectomy apparatus are typically simpler than posterior vitrectomy apparatus and may be used in cataract and other surgical procedures which are performed at the front of the eye. Although various standalone posterior vitrectomy apparatus exist, there exist very few standalone anterior vitrectomy apparatus. These anterior vitrectomy apparatus may exhibit poor performance specs (800 cuts per minute or less, absent basic fluidics control). Most anterior vitrectomy drivers are integrated into large cataract apparatus, as they are usually used in conjunction. As a result, these apparatus may be large and costly.

However, there is a demonstrated global need, particularly in rural settings, for an ultraportable, high-performance, standalone anterior vitrectomy apparatus. Many places which do not have access to cataract apparatus may require that the surgeon use a standalone anterior vitrectomy apparatus which he or she can easily carry or transport.

Accordingly, there is an established need for a portable, compact, standalone anterior vitrectomy apparatus which can be used to cut vitreous humor from a subject's eye.

SUMMARY OF THE INVENTION

The present invention is directed to a portable, compact, standalone anterior vitrectomy apparatus which can be used to cut vitreous humor from a subject's eye. The anterior vitrectomy apparatus may include a housing which contains or encloses at least some of the functional components of the apparatus. The housing may be sized and configured to fit in the palm of a human hand.

In a first implementation, an anterior vitrectomy apparatus may include: an air compressor, configured to generate compressed air; a pressure reservoir, configured to store compressed air received from the air compressor; a regulator, configured to vary a delivery of compressed air from the air compressor to the pressure reservoir to adjust air pressure within the pressure reservoir; a speed control switch; an air control valve, configured to receive compressed air from the pressure reservoir and to produce pulses of compressed air in accordance with a selective adjustment of the speed control switch; and an air tubing connector, configured to receive the pulses of compressed air from the air control valve. The anterior vitrectomy apparatus may further include an air tubing, connectable to the air tubing connector, and a handheld vitrectomy cutter, connectable to the air tubing to receive the pulses of compressed air from the air control valve via the air tubing connector and the air tubing. A processor may controllably interface with the speed control switch. The processor may include a memory storing software instructions configured to cause the processor to execute the operation of producing an operation of the air control valve through the speed control switch such that the air control valve delivers said pulses of compressed air to the air tubing connector to drive the handheld vitrectomy cutter. The anterior vitrectomy apparatus may further include a housing containing the air compressor, the pressure reservoir, the regulator, the air control valve, and the processor, the housing sized to fit in and be held by a human hand. The air tubing connector and the speed control switch may be arranged on an exterior of the housing.

In a second aspect, the anterior vitrectomy apparatus may further include a release valve, contained inside the housing. The release valve may be configured to selectively exhaust compressed air from between the compressor and the regulator. The processor may controllably interface with the release valve and may be configured to cause the release valve to exhaust compressed air from between the air compressor and the regulator in the absence of said operation of the air control valve by the processor.

In another aspect, the anterior vitrectomy apparatus may further include a pressure sensor, contained inside the housing. The pressure sensor may be configured to sense air pressure between the air compressor and the regulator. The processor may controllably interface with the pressure sensor and may be configured to cause the release valve to exhaust compressed air from between the air compressor and the regulator when the processor detects a pressure sensing by the pressure sensor between the air compressor and the regulator greater than a predetermined threshold, in the absence of said operation of the air control valve by the processor.

In another aspect, the predetermined threshold may be about zero.

In another aspect, the processor may be configured to cause the release valve not to exhaust compressed air from between the air compressor and the regulator during said operation of the air control valve by the processor.

In yet another aspect, the anterior vitrectomy apparatus may further include a pressure gauge inside the housing. The pressure gauge may interface with the processor and the pressure reservoir and may be configured to indicate pressure of air in the pressure reservoir to the processor.

In another aspect, the anterior vitrectomy apparatus may further include a syringe connectable to the handheld vitrectomy cutter to suction and collect vitreous humor from the handheld vitrectomy cutter.

In another aspect, the anterior vitrectomy apparatus may further include a foot pedal connector on the exterior of the housing. The foot pedal connector may be configured for the coupling thereto of a foot pedal external to the housing such that the foot pedal connector connects the foot pedal to the processor to facilitate said operation of the air control valve.

In another aspect, the speed control switch may include a rotatable dial.

In yet another aspect, the anterior vitrectomy apparatus may further include a reset button on housing. The reset button may be configured to facilitate a resetting of the processor.

In another aspect, the anterior vitrectomy apparatus may further include a peristaltic pump and a vacuum line. The peristaltic pump may be located inside the housing. The vacuum line may provide fluid communication between the peristaltic pump and the handheld vitrectomy cutter to suction and collect vitreous humor from the handheld vitrectomy cutter.

In another aspect, the peristaltic pump may be driven by a stepper motor driver located inside the housing and interfacing with the processor.

In another aspect, the anterior vitrectomy apparatus may further include a vacuum sensor in fluid communication with the vacuum line and configured to provide a measurement of air vacuum pressure in the vacuum line to the processor.

In yet another aspect, the anterior vitrectomy apparatus may further include an air pump and air tubing. The air pump may be located inside the housing and may be configured to provide pressurized air. The air tubing may provide fluid communication between the air pump and an infusion line external to the housing and may be configured to be inserted into a subject's eye.

In another aspect, the anterior vitrectomy apparatus may further include a pinch valve, a pinch valve tube and an infusion line. The pinch valve may be located inside the housing. The infusion line may be configured to be inserted into a subject's eye. The pinch valve tube may provide fluid communication between a source of irrigation fluid and the infusion line through the pinch valve.

In another aspect, the source of irrigation fluid may be configured to feed irrigation fluid to the pinch valve by gravity.

In another aspect, the anterior vitrectomy apparatus may further include an air pump and air tubing. The air pump may be located inside the housing and may be configured to provide pressurized air. The air tubing may provide fluid communication between the air pump and the infusion line.

In yet another aspect, the anterior vitrectomy apparatus may further include a light source and a fiber-optic cable. The light source may be arranged inside the housing. The fiber-optic cable may be configured to transport light emitted by the light source to a fiber-optic handpiece external to the housing and configured to be inserted into a subject's eye.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

Figure 1:
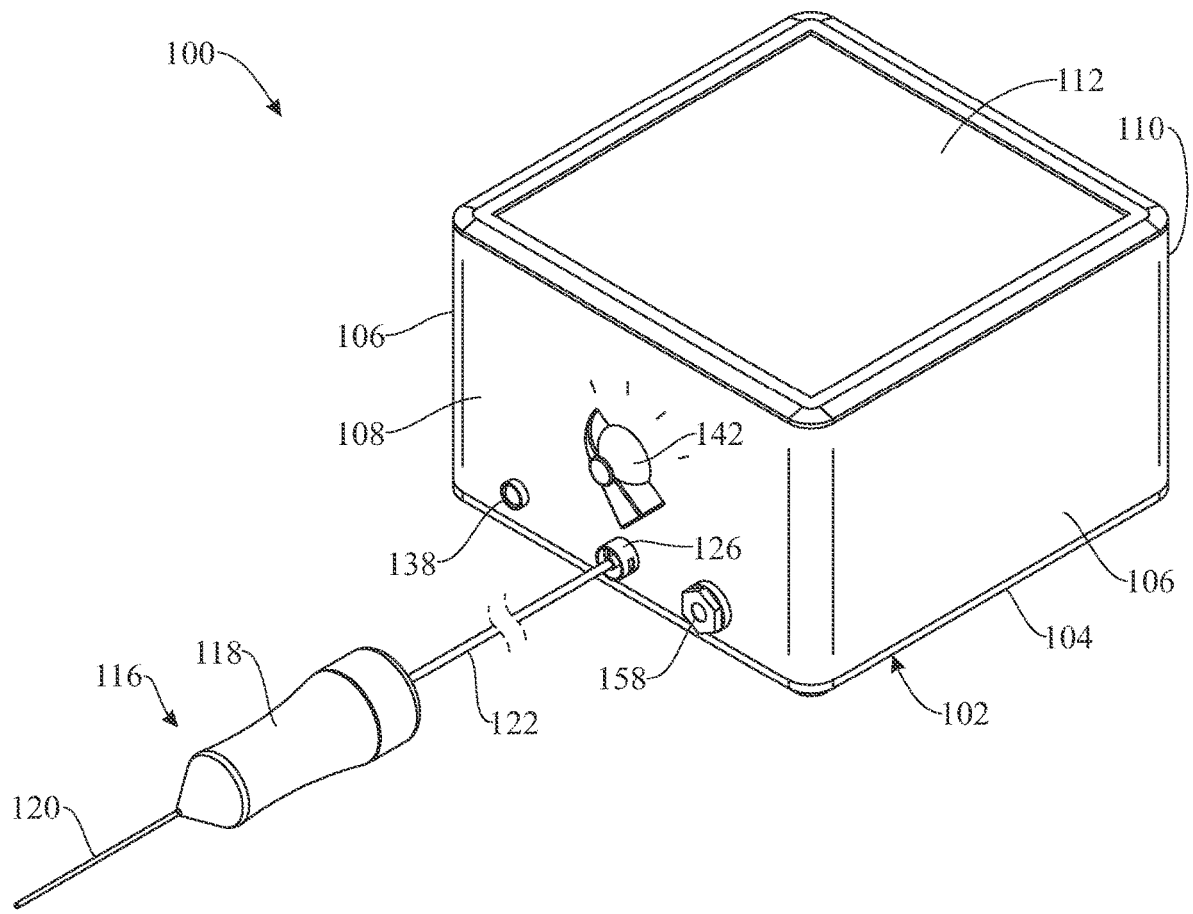
FIG. 1 presents a top front isometric view of an anterior vitrectomy apparatus in accordance with a first illustrative embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a portable, compact, standalone anterior vitrectomy apparatus which can be used to cut vitreous humor from a subject's eye.

Referring initially to FIGS. 1-5, a first illustrative embodiment of the anterior vitrectomy apparatus is generally indicated by reference numeral 100. The anterior vitrectomy apparatus 100 may include a housing 102 which contains or encloses at least some of the functional components of the anterior vitrectomy apparatus 100. The housing 102 may have a size and configuration which render the housing 102 amenable to being comfortably and securely held in the palm of one hand. In some embodiments, the housing 102 may include a housing bottom panel 104 and a housing top panel 112 disposed in parallel, spaced-apart relationship to each other. A pair of parallel, spaced-apart housing side panels 106 may extend between the housing bottom panel 104 and the housing top panel 112 at opposite left and right sides of the housing 106, as shown. A housing front panel 108 and a housing rear panel 110 may extend between the housing bottom panel 104 and the housing top panel 112 and between the housing side panels 106.

As shown in FIG. 1, an air tubing connector 126 may be provided on the exterior of the housing 102, such as on the housing front panel 108, as shown. Air tubing 122 may be connectable to the air tubing connector 126. A handheld vitrectomy cutter 116 may be connectable to the air tubing 122. In some embodiments, the vitrectomy cutter 116 may have a conventional design known by those skilled in the art. The vitrectomy cutter 116 may include a handpiece 118 which is connectable to the air tubing 122. An air-driven oscillation motor (not illustrated) may be provided in the handpiece 118. A reciprocating cutting blade 120 may extend from the handpiece 118. The cutting blade 120 may be operably engaged by the oscillation motor to reciprocate the oscillation motor responsive to air actuation.

Figure 4:
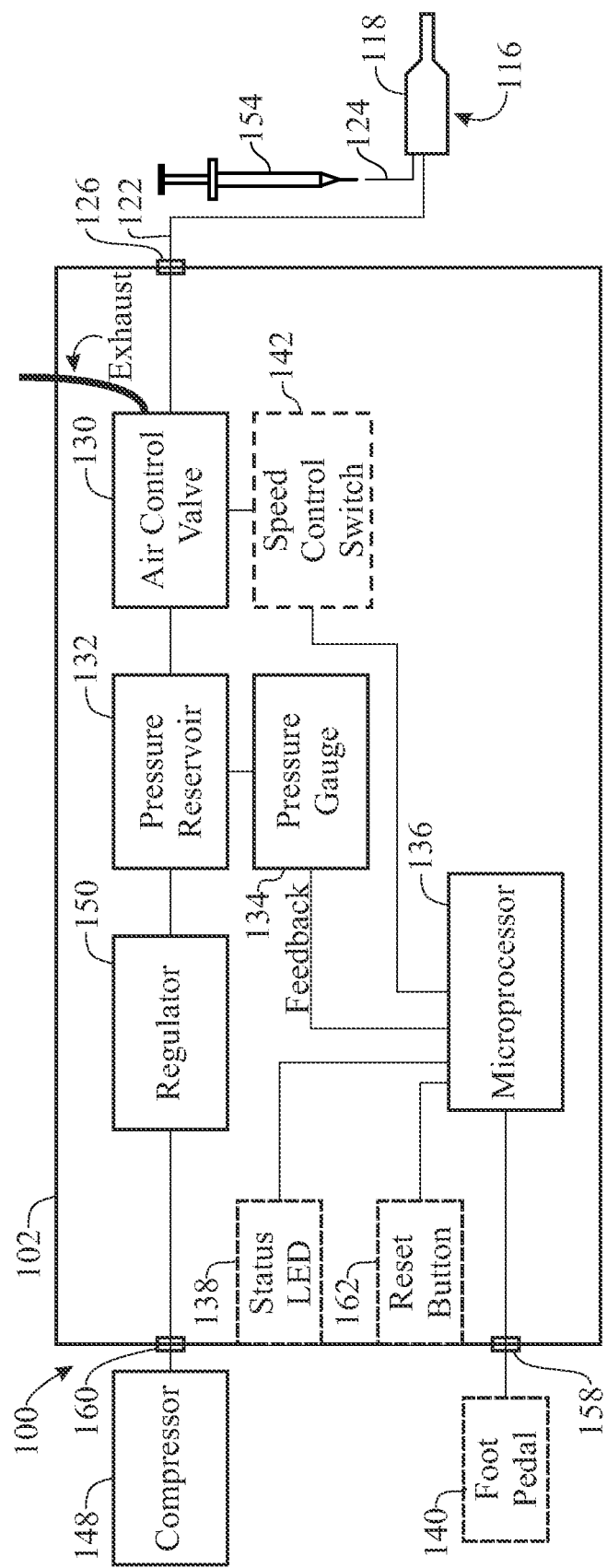
FIG. 4 presents a functional block diagram of the anterior vitrectomy apparatus of FIG. 1.
Figure 5:
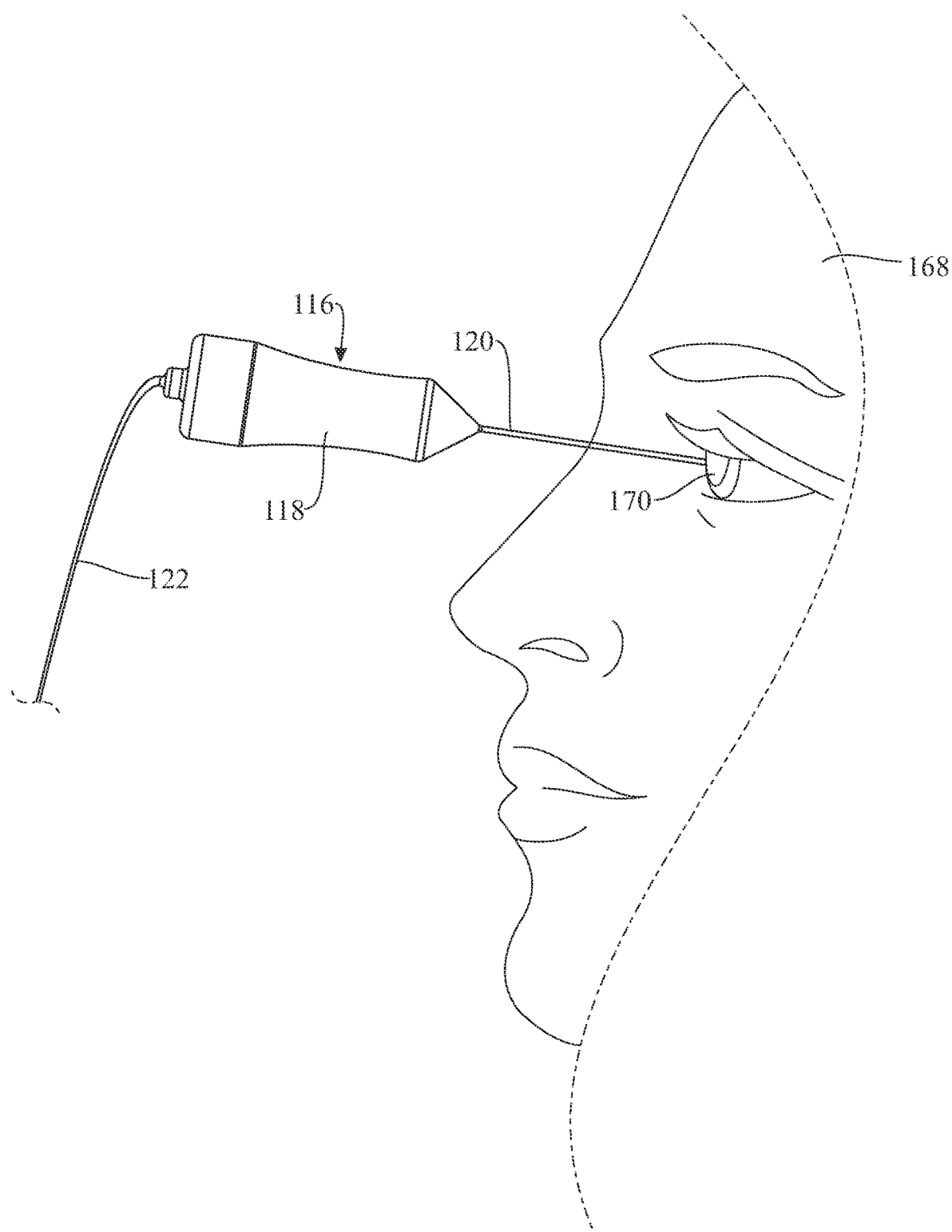
FIG. 5 presents a side view of the vitrectomy cutter of the anterior vitrectomy apparatus of FIG. 1, more particularly illustrating use of the vitrectomy cutter to remove vitreous humor from the eye of a patient in typical application of the anterior vitrectomy apparatus.

As illustrated in FIG. 4, in some embodiments, a syringe 154 may be connectable to the vitrectomy cutter 116 through a syringe tubing 124. In typical application of the anterior vitrectomy apparatus 100, which will be hereinafter described, the syringe 154 may be operated to create a vacuum or suction on the syringe tubing 124 in order to draw vitreous humor to the syringe, and thereby facilitate collection of vitreous humor removed from the eye 170 of a patient 168 through the cutting blade 120 of the vitrectomy cutter 116, as illustrated in FIG. 5.

As illustrated in FIG. 4, an air control valve 130, pressure reservoir 132 and regulator 150 may be provided in the housing 102. The air control valve 130 may communicate with the vitrectomy cutter 116 through the air tubing 122. In turn, the pressure reservoir 132 may communicate with the air control valve 130. The regulator 150 may communicate with the pressure reservoir 132 and may be configured to regulate the pressure of air provided to the pressure reservoir 132 so that the pressure of air within the pressure reservoir 132 is maintained at a desired level (e.g., 30 PSI).

Figure 2:
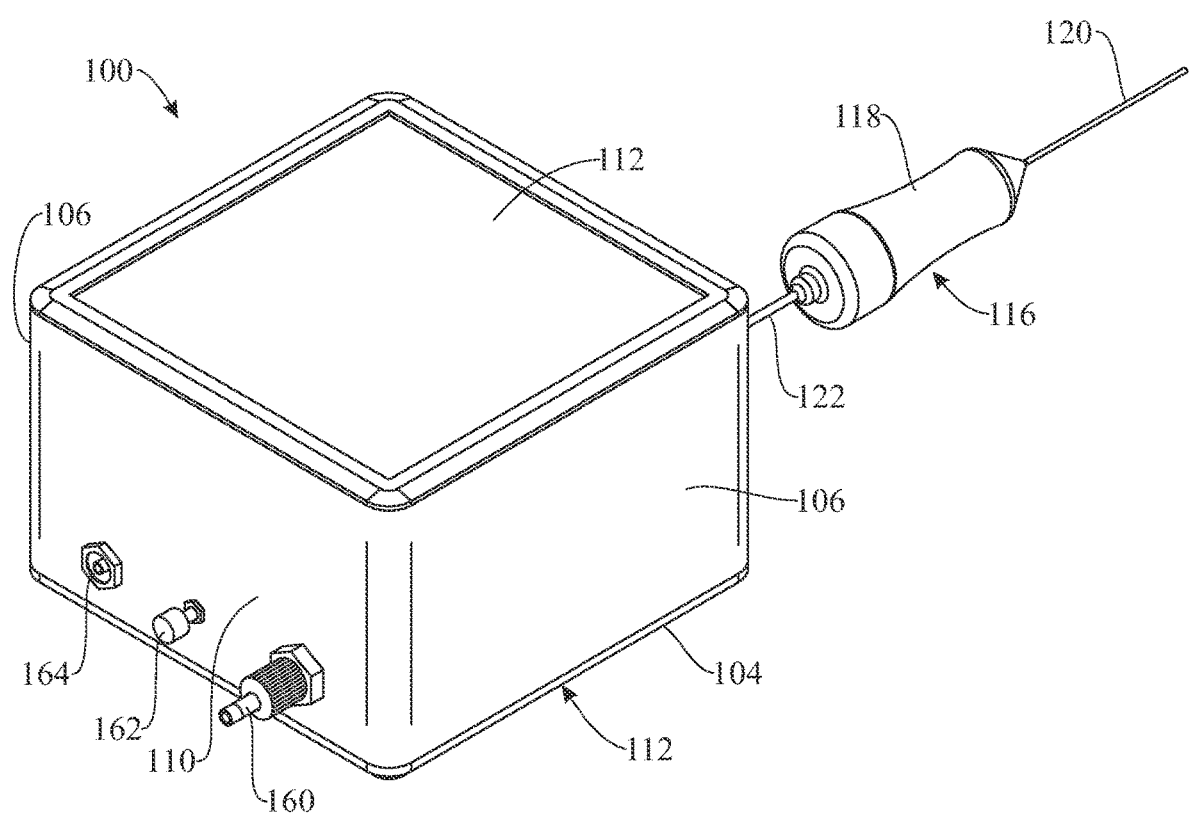
FIG. 2 presents a top rear isometric view of the anterior vitrectomy apparatus of FIG. 1.

As illustrated in FIG. 2, an air compressor connector 160 may be provided on the exterior of the housing 102. The air compressor connector 160 may communicate with the regulator 150 in the housing 102. The air compressor connector 160 may be configured for connection to an air compressor 148 (FIG. 4) outside the housing 102 in operation of the anterior vitrectomy apparatus 100, which will be hereinafter described. For instance and without limitation, the air compressor 148 may be a conventional type of compressor which is used to supply a source of compressed air in vitrectomy procedures. In some embodiments, the air compressor connector 160 may be a quick-disconnect connector known by those skilled in the art.

Figure 3:
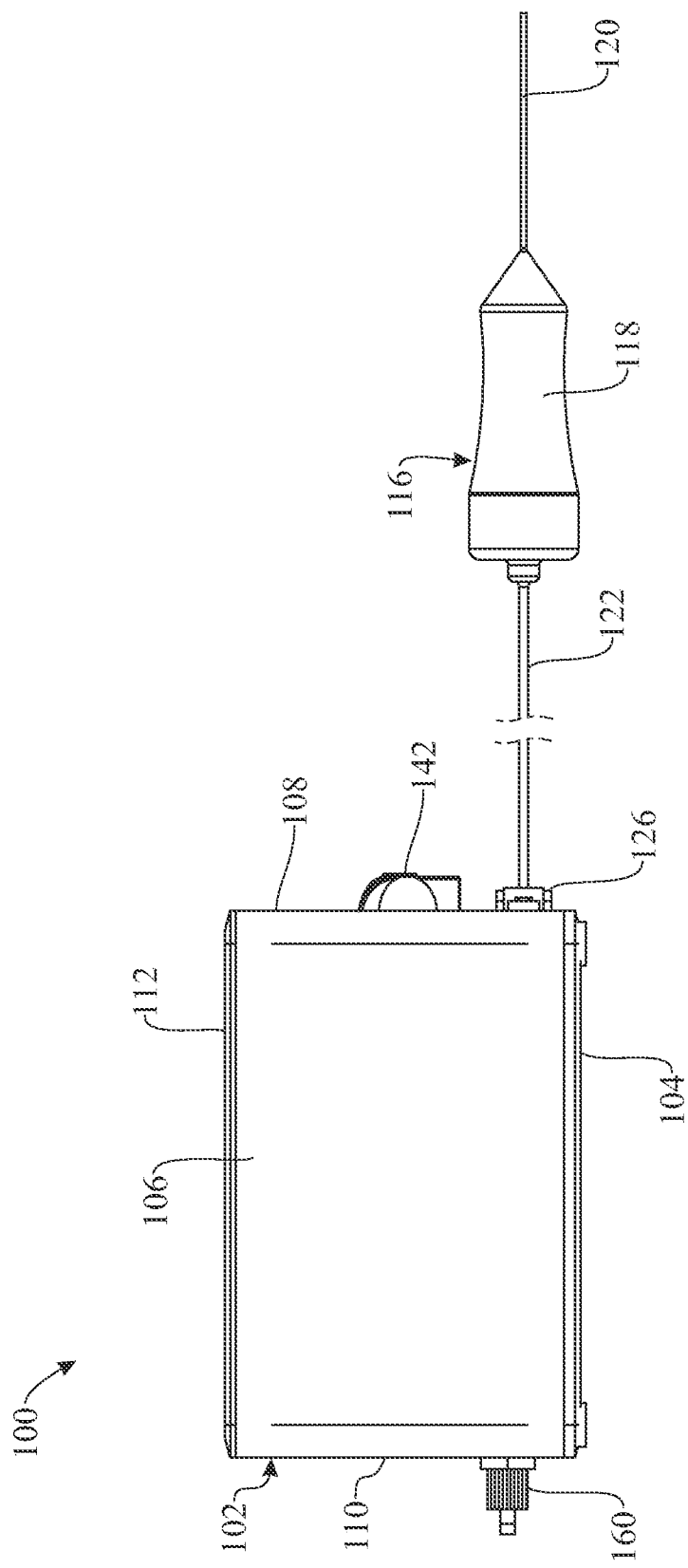
FIG. 3 presents a left side elevation view of the anterior vitrectomy apparatus of FIG. 1.

As illustrated in FIGS. 1 and 3, a speed control switch 142 may be provided on the exterior of the housing 102. The illustration of FIG. 4, which shows user-operable and/or user interface components in broken lines, shows that the speed control switch 142 may controllably interface with the air control valve 130. The speed control switch 142 may enable the operator of the anterior vitrectomy apparatus 100 to adjust the reciprocating speed of the cutting blade 120 of the vitrectomy cutter 116 appropriately. In some embodiments, the speed control switch 142 may include a rotatable dial which is selectively positional to various CPM (cuts per minute) values such as 100, 600, 1200 and 2000, for example and without limitation.

As further shown in FIG. 4, a pressure gauge 134 may be provided in the housing 102. The pressure gauge 134 may communicate with the pressure reservoir 132 to measure the pressure of air therein. The pressure gauge 134 may be configured to indicate the pressure of air in the pressure reservoir 132. A microprocessor 136 or other processing unit (which may include a memory storing software instructions to be executed by the microprocessor 136 or other processing unit) may controllably interface with the speed control switch 142 and may interface with the pressure gauge 134. The microprocessor 136 may be programmed to control the air control valve 130 through the speed control switch 142 such that the air control valve 130 delivers pulses of air from the pressure reservoir 132 through the air control valve 130 to drive the vitrectomy cutter 116.

As illustrated in FIG. 2, a power input port 164 may be provided on the exterior of the housing 102, such as on the housing rear panel 110. The power input port 164 may be connected to the microprocessor 136. The power input port 164 may be configured to receive a power cord (not illustrated) which may be connectable to a standard 120- or 240-volt power outlet (not illustrated) or other applicable electrical power source.

As further shown in FIGS. 1 and 4, in some embodiments, at least one status LED 138 may be provided on the exterior of the housing 102. The status LED 138 may be configured to provide a visual indication informative of the operational status of the anterior vitrectomy apparatus 100. For example, the status LED 138 may illuminate a first color, such as green, to indicate a "ready to operate" status (e.g., a status in which pressure of air indicated by the pressure gauge is within a first or normal range); a second color, such as red, to indicate a "excessively-high pressure" status (e.g., a status in which pressure of air indicated by the pressure gauge is higher than a first threshold, wherein the first threshold is greater than or equal to the first range); and a third color, such as blue, to indicate a "excessively-low pressure" status (e.g., a status in which pressure of air indicated by the pressure gauge is lower than a second threshold, wherein the second threshold is less than or equal to the first range). Alternative embodiments are contemplated in status LED may illuminate in different colors and/or illumination patterns (e.g., continuous, flashing, etc.) to provide additional feedback regarding operation or status of the apparatus.

As illustrated in FIG. 4, in some embodiments, a foot pedal 140, external to the housing 102, may be controllably connectable to the microprocessor 136, typically through a foot pedal connector 158 (FIG. 1). The foot pedal connector 158 can be provided on the housing front panel 108, for instance and without limitation. The foot pedal 140 may facilitate foot operation of the vitrectomy cutter 116 through the air control valve 130 while leaving the user's hands free to operate the handpiece 118 and carry out other tasks. For example, the foot pedal 140 may be configured to selectively operate the air control valve 130 to enable or disable airflow from the pressure reservoir 132 to the vitrectomy cutter 116, to activate or deactivate cutting, respectively.

As illustrated in FIG. 2, in some embodiments, a reset button 162 may be provided on the exterior of the housing 102, such as on the housing rear panel 110. The reset button 162 may operably interface with the microprocessor 136 (FIG. 4) to facilitate resetting of the software run by the microprocessor 136.

In typical application of the anterior vitrectomy apparatus 100, the housing 102 may be easily and securely carried or transported by an operator of the apparatus 100 to a surgery location. As illustrated in FIG. 5, the apparatus 100 may be used to cut and remove vitreous humor from the eye 170 of a subject or patient 168. Accordingly, a power cord (not illustrated) may be inserted in the power input port 164 (FIG. 2) and connected to a standard 120 or 240-volt electrical outlet (not illustrated) or other applicable electrical power source. The air tubing 122 which extends from the vitrectomy cutter 116 may be connected to the air tubing connector 126 (FIG. 1) on the housing 102. In some applications, the foot pedal 140 may be connected to the foot pedal connector 158 on the housing 102 to interconnect the foot pedal 140 to the microprocessor 136. As illustrated in FIG. 4, in some applications, the syringe 154 may be connected to the vitrectomy cutter 116 typically through the syringe tubing 124. The compressor 148 may be connected to the air compressor connector 160 (FIG. 2) on the housing 102, thereby providing fluid communication between the compressor 148 and the regulator 150.

The compressor 148 may be switched on, and compressed air may flow from the compressor 148 through the regulator 150 to the pressure reservoir 132. Responsive to input from the pressure gauge 134, the microprocessor 136 may monitor the pressure of the air in the pressure reservoir 132 and energize or illuminate the status LED 138 accordingly. For example, the microprocessor 136 (FIG. 4) may initially energize and illuminate the status LED 138 in the color green, which may indicate the "ready to operate" status of the anterior vitrectomy apparatus 100.

By manipulation of the speed control switch 142 on the housing 102, the operator of the anterior vitrectomy apparatus 100 may select the desired operational speed of the vitrectomy cutter 116. The operator may then depress the foot pedal 140 to cause the microprocessor 136, controlled by the supporting software, to open the air control valve 130 to a position and at a rate and timing which cause compressed air from the pressure reservoir 132 to flow in pulses of air that drive the vitrectomy cutter 116 through the air tubing 122. The desired operational speed of the vitrectomy cutter 116 may be set using the speed control switch 142.

With reference to FIG. 5, the operator may grip the vitrectomy cutter 116 at the handpiece 118 and direct the tip of the cutting blade 120 through the front of the eye 170 of the patient 168 and into the vitreous humor in the interior of the eye 170. At the vitrectomy cutter 116, the compressed air may flow from the air tubing 122 into the handpiece 118 and the oscillation motor (not illustrated) inside the handpiece 118. The oscillation motor may reciprocate the cutting blade 120 with respect to the handpiece 118. Simultaneously, the syringe 154 (FIG. 4) may be operated to draw the vitreous humor from the patient's eye 170 through the syringe tubing 124 into the syringe 154.

After the desired quantity of vitreous humor has been removed from the patient's eye 170, the operator may terminate operation of the vitrectomy cutter 116 by releasing the foot pedal 140. This action may cause the microprocessor 136 to close the air control valve 130, which may prevent further flow of the compressed air from the pressure reservoir 132 through the air control valve 130 to the vitrectomy cutter 116. The operator may then remove the cutting blade 120 from the patient's eye 170 and complete the procedure.

Throughout operation of the vitrectomy cutter 116, the operator may continually receive input from the microprocessor 136, via the status LED 138, which indicates the pressure of air in the pressure reservoir 132. For example and without limitation, in the event that the pressure of air in the pressure reservoir 132 exceeds a predetermined threshold pressure, the microprocessor 136 may illuminate the status LED 138 in the color red, which may indicate damage or malfunction of the unit. In the event that the pressure of air in the pressure reservoir 132 falls below the predetermined threshold pressure, the microprocessor 136 may illuminate the status LED 138 in the color blue, allowing the user to become aware of the low-pressure situation and act accordingly (e.g., by checking that the air compressor 148 is correctly connected to the compressor connector 160, turned on, and set at or above the minimal pressure (e.g., 40 PSI)).

After use of the anterior vitrectomy apparatus 100 is completed, the power cord (not illustrated) may be removed from the power input port 164 (FIG. 2) in the housing 102. The air compressor 148 (FIG. 4) may be disconnected from the air compressor connector 160 on the housing 102. The air tubing 122 may be disconnected from the air tubing connector 126 on the housing 102. The foot pedal 140 may be disconnected from the foot pedal connector 158 (FIG. 1). The housing 102, vitrectomy cutter 116, air tubing 122, air compressor 148 and other components used in operation of the anterior vitrectomy apparatus 100 may be easily stored and carried or transported for use in multiple locations. In some embodiments, the operational software for the microprocessor 136 may be reset by depression of the reset button 162.

Figure 6:
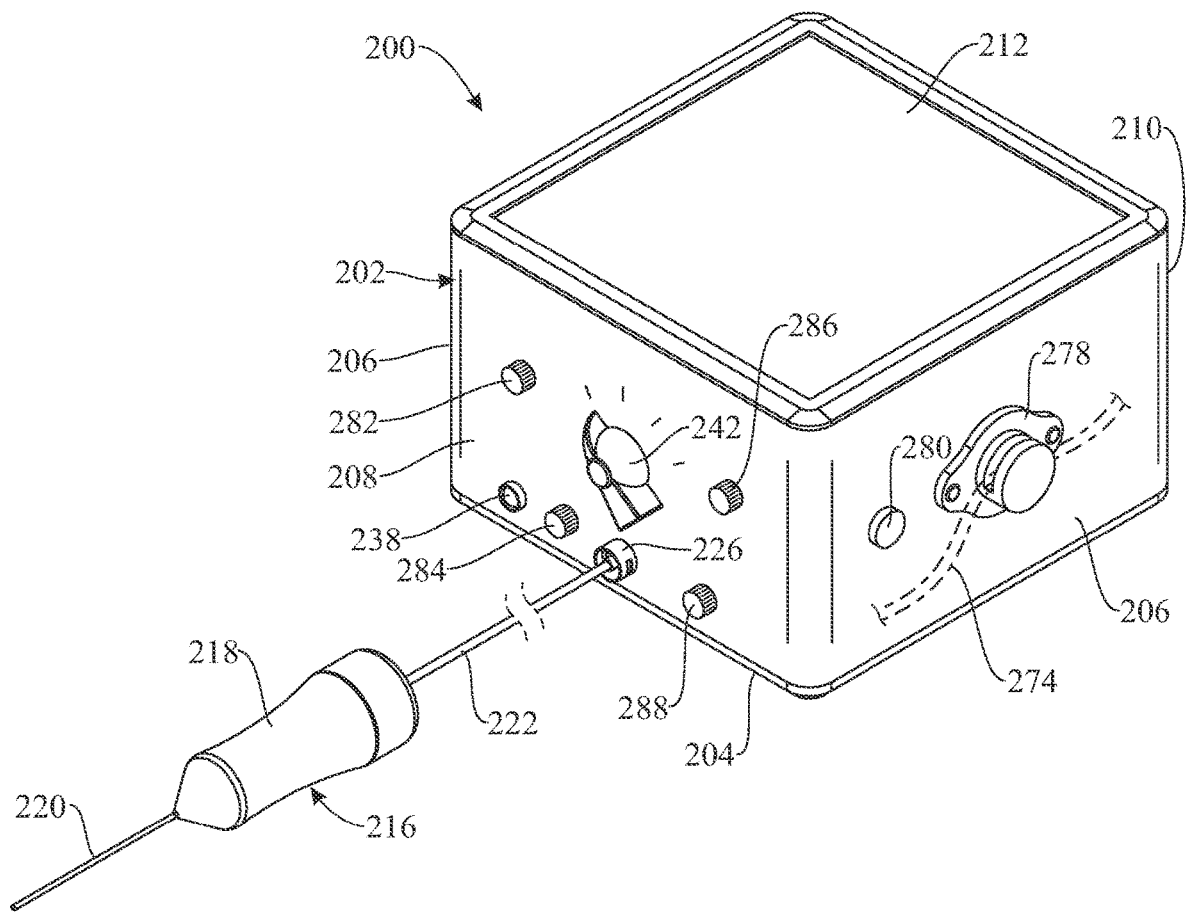
FIG. 6 presents a top front isometric view of an anterior vitrectomy apparatus in accordance with a second illustrative embodiment of the present invention.
Figure 7:
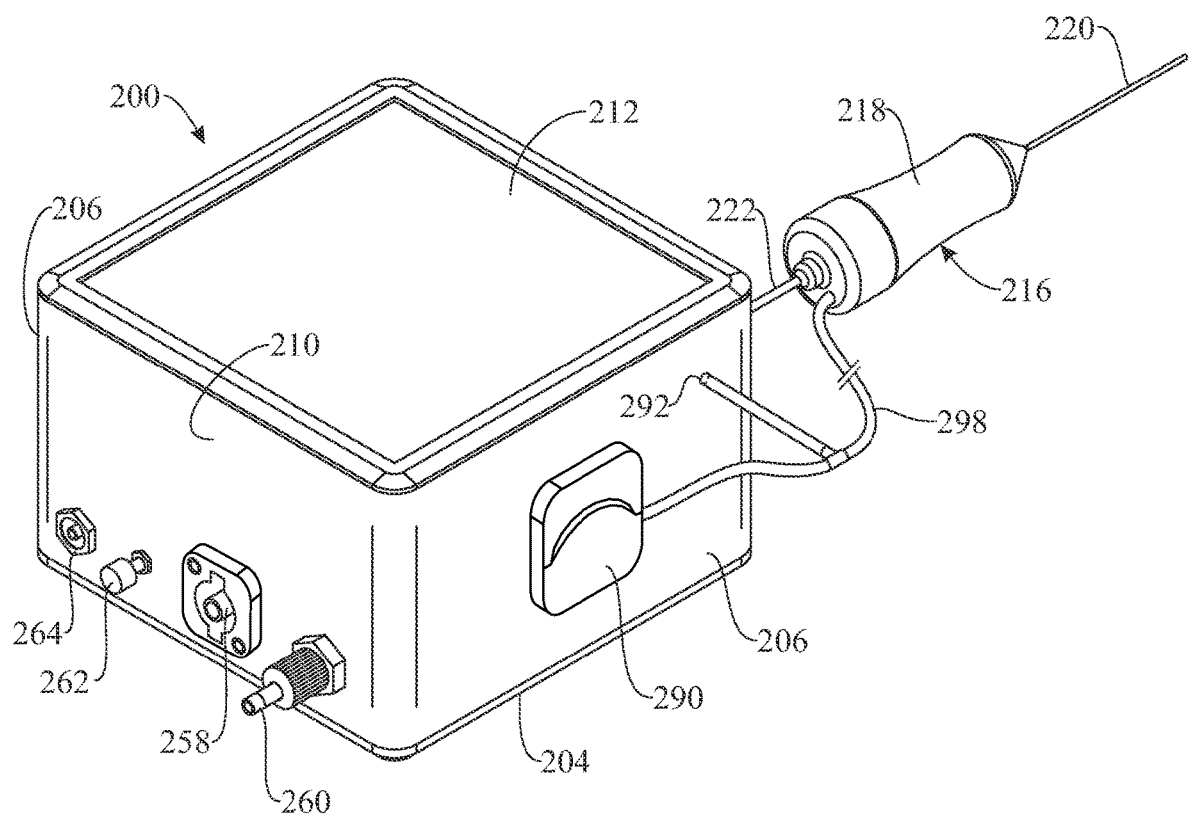
FIG. 7 presents a top rear isometric view of the anterior vitrectomy apparatus of FIG. 6.
Figure 8:
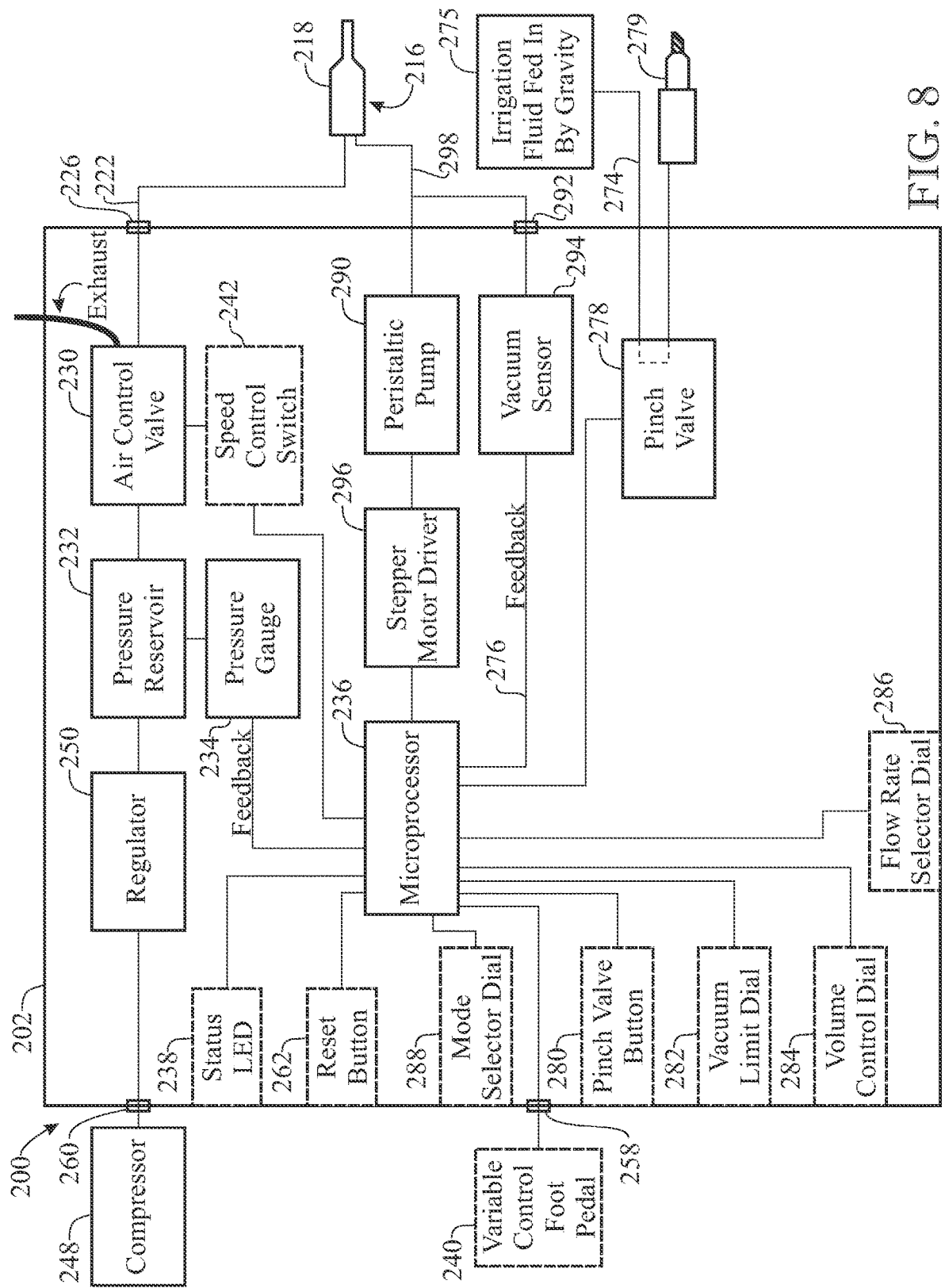
FIG. 8 presents a functional block diagram of the anterior vitrectomy apparatus of FIG. 6.

Referring next to FIGS. 6-8, a second illustrative embodiment of the anterior vitrectomy apparatus of the present invention is generally indicated by reference numeral 200. In the anterior vitrectomy apparatus 200, elements which are analogous to the respective elements of the anterior vitrectomy apparatus 100 that was heretofore described with respect to FIGS. 1-5 are designated by the same respective numerals in the 200-299 series in FIGS. 6-8.

Similarly to the previous embodiment, the anterior vitrectomy apparatus 200 of the present embodiment may include a microprocessor 236, regulator 250, pressure reservoir 232, air control valve 230, and pressure gauge 234 contained within a housing 202 (FIGS. 6 and 7). The housing 202 is compact, manually portable, and, in some embodiments, is small enough to fit in a single hand of a user. The housing 202 may be generally cubic or rectangular and may include housing bottom, side, front, rear and top panels 204, 206, 208, 210 and 212. Also similarly to the previous embodiment, as shown in FIGS. 6 and 7, the anterior vitrectomy apparatus 200 may include an air tubing connector 226, status LED 238, speed control switch 242, air compressor connector 260, reset button 262, power input port 264, and foot pedal connector 258 provided on the housing 202. As with the previous embodiment, a vitrectomy cutter 216 comprising a handpiece 218 and cutting blade 220 may be connected to the air tubing connector 226 via an air tubing 222. An air compressor 248 (FIG. 8) may be connected to the regulator 250 via the air compressor connector 260.

As shown in FIG. 8, in order to collect vitreous humor removed from the eye of a patient, the present embodiment includes a peristaltic vacuum pump 290 that communicates with the vitrectomy cutter 216 through a vacuum line 298. As illustrated in FIG. 7, in some embodiments, the peristaltic vacuum pump 290 may be provided in the housing 202, such as on a housing side panel 206. A stepper motor driver 296 located within the housing 202 may functionally interface with the peristaltic vacuum pump 290. The microprocessor 236 may controllably interface with the stepper motor driver 296. By operation of the peristaltic vacuum pump 290, responsive to actuation by the stepper motor driver 296 via input from the microprocessor 236, the peristaltic vacuum pump 290 may apply vacuum pressure to the vitrectomy cutter 216 through the vacuum line 298.

As further illustrated in FIG. 8, a vacuum sensor 294 located within the housing 202 may interface with the vacuum line 298 through a vacuum sensor connector 292. As shown in FIG. 7, the vacuum sensor connector 292 can be arranged on a housing side panel 206 or other panel of the housing 202, and preferably on the same housing side panel 206 as the peristaltic vacuum pump 290. The microprocessor 236 may communicate with the vacuum sensor 294 through a feedback line 276, shown in FIG. 8. The vacuum sensor 294 may monitor the vacuum pressure in the vacuum line 298 through the vacuum sensor connector 292, and may transmit vacuum pressure feedback which corresponds to the measured vacuum pressure to the microprocessor 236. Responsive to the vacuum pressure feedback, the microprocessor 236 may modulate the operational speed of the peristaltic vacuum pump 290, and hence, the vacuum pressure in the vacuum line 298 through the stepper motor driver 296.

As illustrated in FIG. 6, in some embodiments, a pinch valve 278 may be provided on the housing 202, such as on a housing side panel 206 opposite to the housing side panel 206 on which the peristaltic vacuum pump 290 is located. A flexible pinch valve tube 274, which may be made from silicone, for example and without limitation, may extend through the pinch valve 278. The pinch valve 278 may normally be disposed in a closed configuration in which the pinch valve 278 closes or pinches the pinch valve tube 274. An irrigation fluid supply by gravity 275 may communicate with an inlet end of the pinch valve tube 274. The pinch valve tube 274 may discharge into the eye through a sleeve alongside the cutting blade 220 of the vitrectomy cutter 216 or another separate channel or infusion line (as shown in FIG. 8), as known in the art. A variable control foot pedal 240 (FIG. 8) may operationally interface with the pinch valve 278. Accordingly, responsive to depression of the variable control foot pedal 240, the pinch valve 278 may open and release the pinch valve tube 274 so that fluid is allowed to flow through the pinch valve tube 274. Consequently, irrigation fluid may flow from the irrigation fluid supply by gravity 275 through the pinch valve tube 274 and discharge through the sleeve parallel to the cutting blade 220 or another separate channel or infusion line 279, as shown, to irrigate the eye 170 to maintain pressure in the eye 170 and prevent collapse.

As further illustrated in FIG. 6, a pinch valve button 280 may be provided on the housing 202, such as on the same housing side panel 206 as the pinch valve 278. The pinch valve button 280 may operably interface with the pinch valve 278 in such a manner that upon first depression of the pinch valve 278, the pinch valve button 280 is permanently open for continuous irrigation of the eye 170 through the pinch valve tube 274 such that the operator need not continually depress the variable control foot pedal 240. Upon second depression of the pinch valve 278, the pinch valve 278 may permanently close to prevent irrigation of the eye 170.

As illustrated in FIGS. 5 and 8, a vacuum limit dial 282 on the housing 202 may interface with the microprocessor 236. The vacuum limit dial 282 may facilitate selection of the maximum value, magnitude or level of vacuum pressure which the peristaltic vacuum pump 290 (FIG. 8) applies to the vitrectomy cutter 216 through the vacuum line 298. The vacuum limit dial 282 may have various settings (such as, but not limited to, four maximum vacuum value settings).

As further illustrated in FIG. 6, a volume control dial 284 on the housing 202 may interface with the microprocessor 236 (FIG. 8). The volume control dial 284 may include an internal tone generator which indicates the various values, magnitudes or levels of vacuum pressure which the peristaltic pump 290 applies to the vitrectomy cutter 216. The volume control dial 284 may be rotated to adjust the volume level of the internal tone generator.

A flow rate selector dial 286 on the housing 202 may interface with the microprocessor 236. The flow rate selector dial 286 may be rotated to select the operational pumping rate of the peristaltic vacuum pump 290 and may have multiple settings ranging from slow to fast.

A mode selector dial 288 on the housing 202 may interface with the microprocessor 236. The mode selector dial 288 may be rotated to select among multiple modes of operation of the anterior vitrectomy apparatus 200. The modes of operation may include: (1) a first mode, in which operation is completely manual (no vacuum pump or irrigation); (2) a second mode, in which operation takes place with vacuum and irrigation only, without cutting; (3) a third mode, in which irrigation occurs first, cutting by the handpiece 218 takes place secondly, and vacuuming by the handpiece 218 takes place thirdly, depending on the degree or depth to which the variable control foot pedal 240 is pressed (e.g., initial pedal engagement starts irrigation, then the first half depression of the variable control foot pedal 240 engages the cutting action of the cutting blade 220, and the second half depression of the variable control foot pedal 240 engages vacuuming); and (4) a fourth mode, in which irrigation occurs first, then the handpiece 218 vacuums second, and then the handpiece 218 cuts third, depending on the degree or depth to which the variable control foot pedal 240 is pressed (e.g., initial pedal engagement starts irrigation, then the first half depression of the variable control foot pedal 240 engages vacuuming, and the second half depression of the variable control foot pedal 240 engages the cutting action of the cutting blade 220). For the purpose of executing the aforementioned third and fourth modes, the variable control foot pedal 240 may include a momentary switch that activates irrigation upon slightly pressing the variable control foot pedal 240, and a potentiometer which is engaged when further depression of the variable control foot pedal 240 occurs, in order to activate cutting and vacuuming in the order corresponding to the specific mode and in dependence of the degree of compression of the variable control foot pedal 240.

Application of the anterior vitrectomy apparatus 200 may be similar to that which was heretofore described with respect to the anterior vitrectomy apparatus 100 in FIGS. 1-5. The peristaltic vacuum pump 290 (FIG. 8) may be operated to vacuum the vitreous humor from the eye 170 (FIG. 5) of the patient 168. The pinch valve 278, pinch valve button 280, vacuum limit dial 282, volume control dial 284, flow rate selector dial 286 and mode selector dial 288 may be manipulated to control various operational parameters of the peristaltic vacuum pump 290, typically as was heretofore described.

Figure 9:
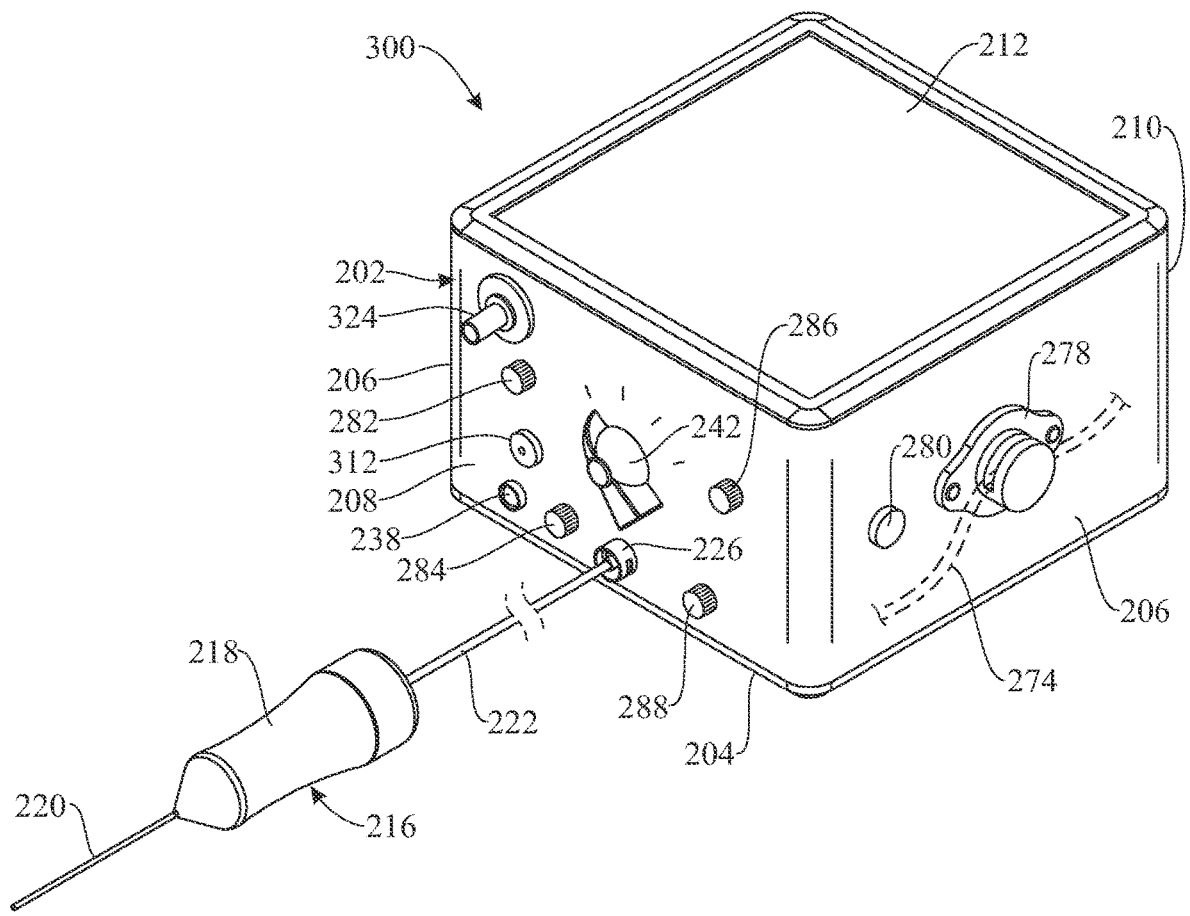
FIG. 9 presents a top front isometric view of an anterior vitrectomy apparatus in accordance with a third illustrative embodiment of the present invention.
Figure 10:
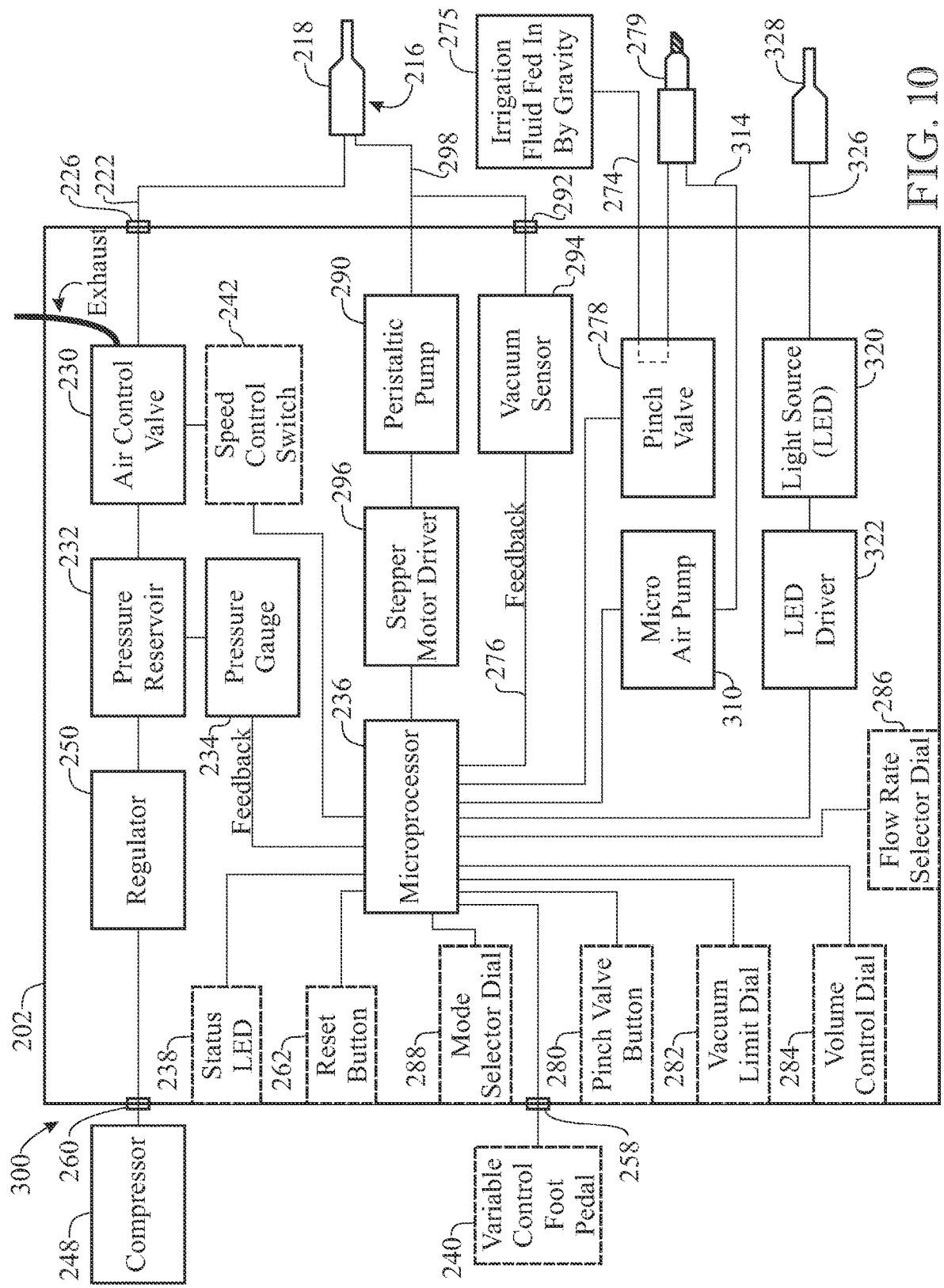
FIG. 10 presents a functional block diagram of the anterior vitrectomy apparatus of FIG. 9.

The illustrations of FIGS. 9 and 10 show an anterior vitrectomy apparatus 300 in accordance with a third illustrative embodiment of the present invention. The anterior vitrectomy apparatus 300 is analogous to the anterior vitrectomy apparatus 200, and further includes a micro air pump 310 in the housing 202. The micro air pump 310 is provided in fluid communication with an air tubing connector 312 on the housing 202, such as on the housing front panel 208. An external air tubing 314 (FIG. 10) may be connected to the air tubing connector 312 and may provide fluid communication between the air tubing connector 312 and a line configured to be introduced into the eye. For instance, an air tubing 314 may connect the air tubing connector 312 to the same line that is providing fluid irrigation into the eye via the pinch valve 278 (e.g., through the sleeve parallel to the cutting blade 220 or another separate channel or infusion line 279, as shown). The micro air pump 310 may generate pressurized air and pump the pressurized air, via the air tubing connector 312, to the external air tubing 314 and into the eye.

The anterior vitrectomy apparatus 300 further comprises an internal light source or LED 320 controlled by a LED driver 322. The LED 320 provides a source of light at a light connector 324 on the housing 202, such as on the housing front panel 208. A fiber-optic cable 326 (FIG. 10) may be coupled to or plugged into the light connector 324. A fiber optic handpiece 328 or light pipe may be coupled to the fiber-optic cable 326 and may be inserted into the eye, illuminating the eye from the inside when the LED 320 is activated by the LED driver 322 during operation of the anterior vitrectomy apparatus 300.

Figure 11:
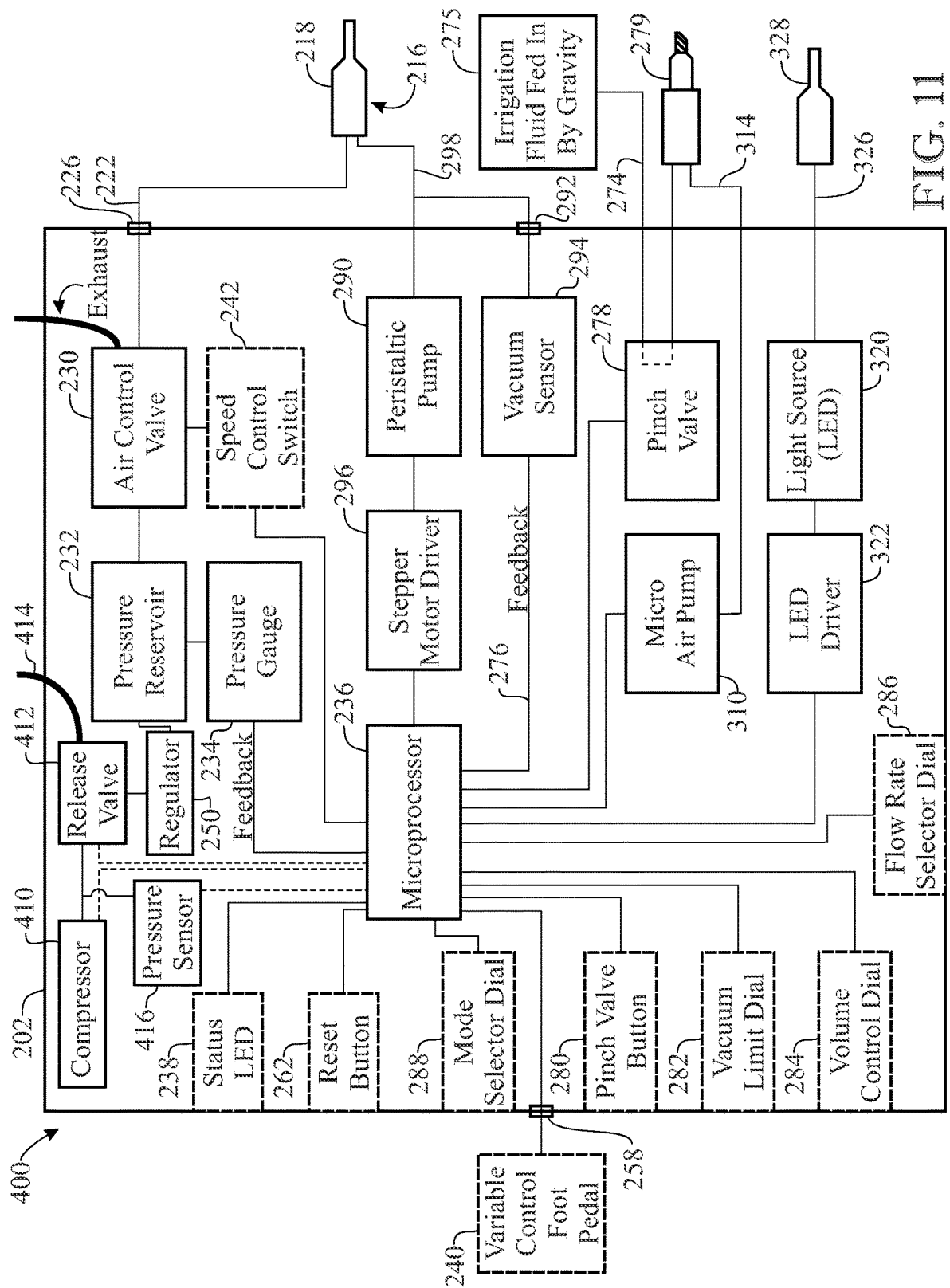
FIG. 11 presents a functional block diagram of an anterior vitrectomy apparatus in accordance with a third illustrative embodiment of the present invention, comprising an internal air compressor, pressure sensor and release valve.

The illustration of FIG. 11 shows an anterior vitrectomy apparatus 400 in accordance with a fourth illustrative embodiment of the present invention. The anterior vitrectomy apparatus 400 of FIG. 11 may be similar to the anterior vitrectomy apparatus 300 shown in FIGS. 9 and 10. For clarity purposes, the same reference numerals are being used in FIG. 11 to indicate components which are similar or identical to those of the anterior vitrectomy apparatus 300 of FIGS. 9 and 10 and prior embodiments shown in prior figures. Similarly to previous embodiments, the anterior vitrectomy apparatus 400 comprises housing 202, which is preferably shaped and sized to fit in a human hand.

The anterior vitrectomy apparatus 400 is however different from the anterior vitrectomy apparatus 300 in several aspects. Firstly, the anterior vitrectomy apparatus 400 lacks an air compressor connector (such as air compressor connector 260 of FIG. 10) and is not configured to be connected to an external air compressor (such as air compressor 248 of FIG. 10). Secondly, the anterior vitrectomy apparatus 400 comprises an air pump or air compressor 410 housed inside or contained within the housing 202. The air compressor 410 may be operatively connected to the microprocessor 236 via one or more electrical control lines, which have been depicted as a single broken line. In some embodiments, the air compressor 410 may be powered by an external power source such as that which powers the microprocessor 236 and other applicable components via the power input port 264 (FIG. 7).

The internal air compressor 248 is configured to provide compressed air to the regulator 250, for the regulator 250 to direct to the pressure reservoir 232 and subsequent components as described heretofore with reference to previous embodiments. In some embodiments, such as the present embodiment, the air compressor 248 may provide compressed air to the regulator 250 via the release valve 412. The release valve 412, which may also be contained within the housing 202, may be configured to release a volume of air outside the housing 202, via an air exhaust 414, in the event of an excessive pressure being sensed by the release valve 412 at the air compressor 410. The release valve 412 may be operatively connected to and controlled by the microprocessor 236 via one or more electrical control lines, which have been depicted as a single broken line. In some embodiments, the release valve 412 may be powered by an external power source such as that which powers the microprocessor 236 and other applicable components via the power input port 264 (FIG. 7).

The anterior vitrectomy apparatus 400 may further include a pressure sensor 416, configured to measure air pressure immediately after the air compressor 410 (or at an output thereof), i.e. between the air compressor 410 and the release valve 412. The pressure sensor 416 may be operatively connected to the microprocessor 236 via one or more electrical control lines, which have been depicted as a single broken line. In some embodiments, the pressure sensor 416 may be powered by an external power source such as that which powers the microprocessor 236 and other applicable components via the power input port 264 (FIG. 7).

In some embodiments, operation of the anterior vitrectomy apparatus 400 with respect to the air compressor 410, release valve 412, and pressure sensor 416, may be as follows. As was heretofore described with reference to the anterior vitrectomy apparatus 200, a user may operate or engage the variable control foot pedal 240 (e.g., according to the third or fourth modes) to initiate cutting by the vitrectomy cutter 216. When the variable control foot pedal 240 is not engaged, or is engaged in a manner not configured to initiate cutting, the microprocessor 236 may monitor the air pressure immediately after the air compressor 410 via the pressure sensor 416; in the event that the air pressure is detected by the pressure sensor 416 to be greater than a predetermined threshold, the microprocessor 236 may responsively open the release valve 412 to cause compressed air to be exhausted via the air exhaust 414. The predetermined threshold is greater than or equal to zero and indicates a slight air compression or no air compression, respectively, and more preferably, is about zero (i.e. about atmospheric air pressure or about zero air compression), In this way, the air compressor 410 is maintained with a low, and more preferably, zero pressure until subsequent engagement of the variable control foot pedal 240 by the user to initiate cutting; i.e. the air compressor 410 is thereby allowed to engage without air pressure resistance. When the variable control foot pedal 240 is engaged in a manner configured to initiate cutting, the microprocessor 236 activates the air compressor 410 and closes the release valve 412 such that air is not exhausted through the air exhaust 414, allowing compressed air from the air compressor 410 to flow generally entirely towards the regulator 250, pressure reservoir 232, and so forth.

The anterior vitrectomy apparatus 400 of the present embodiment may thus be operated without relying on an external gas source, thereby rendering the anterior vitrectomy apparatus 400 more self-contained and easier to carry, transport, store, and operate. Furthermore, with respect to conventional anterior vitrectomy apparatuses in which compressed air is provided by external compressed air canisters, the anterior vitrectomy apparatus 400 provides the additional advantage that it does not require external gas replacement or refilling, and is thus always readily available for use. The anterior vitrectomy apparatus 400 of the present embodiment generally incorporates all or most necessary features into a small and portable unit which may be completely independent of external gas sources.

It should be noted that further embodiments are contemplated in which the anterior vitrectomy apparatus 100 and 200 of the present disclosure are provided with the internal air compressor 410, release valve 412, air exhaust 414 and pressure sensor 416, and associated methods of operation (which may also involve the microprocessor 236) as heretofore described with reference to the anterior vitrectomy apparatus 400.

It will be appreciated by those skilled in the art that the anterior vitrectomy apparatus 100, 200, 300, 400 is capable of being advantageously used, for instance, in rural settings where cataract apparatus are often needed but not available. The anterior vitrectomy apparatus 100, 200, 300, 400 can provide optimum performance specifications (cut rate of 2000+ cuts per minute, integrated peristaltic pump with linear vacuum control and irrigation control) while fitting in the palm of the hand.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. An anterior vitrectomy apparatus, comprising:
    an air compressor, configured to generate compressed air;
    a pressure reservoir, configured to store compressed air received from the air compressor;
    a regulator, configured to vary a delivery of compressed air from the air compressor to the pressure reservoir to adjust air pressure within the pressure reservoir;
    a speed control switch;
    an air control valve, configured to receive compressed air from the pressure reservoir and to produce pulses of compressed air in accordance with a selective adjustment of the speed control switch;
    an air tubing connector, configured to receive said pulses of compressed air from the air control valve;
    an air tubing, connectable to the air tubing connector;
    a handheld vitrectomy cutter, connectable to the air tubing to receive said pulses of compressed air from the air control valve via the air tubing connector and the air tubing;
    a processor controllably interfacing with the speed control switch, the processor comprising a memory storing software instructions configured to cause the processor to execute the operation of:
        producing an operation of the air control valve through the speed control switch such that the air control valve delivers said pulses of compressed air to the air tubing connector to drive the handheld vitrectomy cutter; and
    a housing containing the air compressor, the pressure reservoir, the regulator, the air control valve, and the processor, wherein the housing is sized to fit in and be held by a human hand, and further wherein the air tubing connector and the speed control switch are arranged on an exterior of the housing.

2. The anterior vitrectomy apparatus of claim 1, further comprising a release valve, the release valve contained inside the housing and configured to selectively exhaust compressed air from between the compressor and the regulator, wherein the processor controllably interfaces with the release valve and is configured to cause the release valve to exhaust compressed air from between the air compressor and the regulator in the absence of said operation of the air control valve by the processor.

3. The anterior vitrectomy apparatus of claim 2, further comprising a pressure sensor, the pressure sensor contained inside the housing and configured to sense air pressure between the air compressor and the regulator, wherein the processor controllably interfaces with the pressure sensor and is configured to cause the release valve to exhaust compressed air from between the air compressor and the regulator when the processor detects a pressure sensing by the pressure sensor between the air compressor and the regulator in the absence of said operation of the air control valve by the processor, the pressure sensing greater than a predetermined threshold.

4. The anterior vitrectomy apparatus of claim 3, wherein the predetermined threshold is about zero.

5. The anterior vitrectomy apparatus of claim 2, wherein the processor is configured to cause the release valve not to exhaust compressed air from between the air compressor and the regulator during said operation of the air control valve by the processor.

6. The anterior vitrectomy apparatus of claim 1, further comprising a pressure gauge inside the housing, the pressure gauge interfacing with the processor and the pressure reservoir and configured to indicate pressure of air in the pressure reservoir to the processor.

7. The anterior vitrectomy apparatus of claim 1, further comprising a syringe connectable to the handheld vitrectomy cutter to suction and collect vitreous humor from the handheld vitrectomy cutter.

8. The anterior vitrectomy apparatus of claim 1, further comprising a foot pedal connector on the exterior of the housing, the foot pedal connector configured for the coupling thereto of a foot pedal external to the housing such that the foot pedal connector connects the foot pedal to the processor to facilitate said operation of the air control valve.

9. The anterior vitrectomy apparatus of claim 1, wherein the speed control switch comprises a rotatable dial.

10. The anterior vitrectomy apparatus of claim 1, further comprising a reset button on housing, the reset button configured to facilitate a resetting of the processor.

11. The anterior vitrectomy apparatus of claim 1, further comprising a peristaltic pump and a vacuum line, wherein the peristaltic pump is located inside the housing and the vacuum line provides fluid communication between the peristaltic pump and the handheld vitrectomy cutter to suction and collect vitreous humor from the handheld vitrectomy cutter.

12. The anterior vitrectomy apparatus of claim 11, wherein the peristaltic pump is driven by a stepper motor driver located inside the housing and interfacing with the processor.

13. The anterior vitrectomy apparatus of claim 11, further comprising a vacuum sensor in fluid communication with the vacuum line and configured to provide a measurement of air vacuum pressure in the vacuum line to the processor.

14. The anterior vitrectomy apparatus of claim 1, further comprising an air pump and a second air tubing, wherein the air pump is located inside the housing and is configured to provide pressurized air, and the air tubing provides fluid communication between the second air pump and an infusion line external to the housing and configured to be inserted into a subject's eye.

15. The anterior vitrectomy apparatus of claim 1, further comprising a pinch valve, a pinch valve tube and an infusion line, wherein the pinch valve is located inside the housing and the infusion line is configured to be inserted into a subject's eye, and further wherein the pinch valve tube provides fluid communication between a source of irrigation fluid and the infusion line through the pinch valve.

16. The anterior vitrectomy apparatus of claim 15, wherein the source of irrigation fluid is configured to feed irrigation fluid to the pinch valve by gravity.

17. The anterior vitrectomy apparatus of claim 15, further comprising an air pump and a second air tubing, wherein the air pump is located inside the housing and is configured to provide pressurized air, and the air tubing provides fluid communication between the second air pump and the infusion line.

18. The anterior vitrectomy apparatus of claim 1, further comprising a light source and a fiber-optic cable, wherein the light source is arranged inside the housing and the fiber-optic cable is configured to transport light emitted by the light source to a fiber-optic handpiece external to the housing and configured to be inserted into a subject's eye.

19. An anterior vitrectomy apparatus, comprising:
an air compressor, configured to generate compressed air;
a pressure reservoir, configured to store compressed air received from the air compressor;
a regulator, configured to vary a delivery of compressed air from the air compressor to the pressure reservoir to adjust air pressure within the pressure reservoir;
a release valve, configured to selectively exhaust compressed air from between the compressor and the regulator;
a pressure sensor, configured to sense air pressure between the air compressor and the regulator;
a speed control switch;
an air control valve, configured to receive compressed air from the pressure reservoir and to produce pulses of compressed air in accordance with a selective adjustment of the speed control switch;
an air tubing connector, configured to receive said pulses of compressed air from the air control valve;
an air tubing, connectable to the air tubing connector;
a handheld vitrectomy cutter, connectable to the air tubing to receive said pulses of compressed air from the air control valve via the air tubing connector and the air tubing;
a processor controllably interfacing with the speed control switch, the processor comprising a memory storing software instructions configured to cause the processor to execute the operation of:
producing an operation of the air control valve through the speed control switch such that the air control valve delivers said pulses of compressed air to the air tubing connector to drive the handheld vitrectomy cutter,
causing the release valve to exhaust compressed air from between the air compressor and the regulator when the processor detects a pressure sensing by the pressure sensor between the air compressor and the regulator in the absence of said operation of the air control valve, the pressure sensing greater than a predetermined threshold, and
causing the release valve not to exhaust compressed air from between the air compressor and the regulator during said operation of the air control valve; and
a housing containing the air compressor, the pressure reservoir, the regulator, the release valve, the pressure sensor, the air control valve, and the processor, wherein the housing is sized to fit in and be held by a human hand, and further wherein the air tubing connector and the speed control switch are arranged on an exterior of the housing.

20. An anterior vitrectomy apparatus, comprising:
an air compressor, configured to generate compressed air;
a pressure reservoir, configured to store compressed air received from the air compressor;
a regulator, configured to vary a delivery of compressed air from the air compressor to the pressure reservoir to adjust air pressure within the pressure reservoir;
a release valve, configured to selectively exhaust compressed air from between the compressor and the regulator;
a pressure sensor, configured to sense air pressure between the air compressor and the regulator,
a speed control switch;
an air control valve, configured to receive compressed air from the pressure reservoir and to produce pulses of compressed air in accordance with a selective adjustment of the speed control switch;
an air tubing connector, configured to receive said pulses of compressed air from the air control valve;
an air tubing, connectable to the air tubing connector;
a handheld vitrectomy cutter, connectable to the air tubing to receive said pulses of compressed air from the air control valve via the air tubing connector and the air tubing;
a processor controllably interfacing with the speed control switch, the processor comprising a memory storing software instructions configured to cause the processor to execute the operation of:
producing an operation of the air control valve through the speed control switch such that the air control valve delivers said pulses of compressed air to the air tubing connector to drive the handheld vitrectomy cutter,
causing the release valve to exhaust compressed air from between the air compressor and the regulator when the processor detects a pressure sensing by the pressure sensor between the air compressor and the regulator in the absence of said operation of the air control valve, the pressure sensing greater than a predetermined threshold of about zero, and
causing the release valve not to exhaust compressed air from between the air compressor and the regulator during said operation of the air control valve; and a housing containing the air compressor, the pressure reservoir, the regulator, the release valve, the pressure sensor, the air control valve, and the processor, wherein the housing is sized to fit in and be held by a human hand, and further wherein the air tubing connector and the speed control switch are arranged on an exterior of the housing.

* * * * *